(12) United States Patent
Boime

(10) Patent No.: US 6,225,449 B1
(45) Date of Patent: May 1, 2001

(54) HORMONE ANALOGS WITH MULTIPLE CTP EXTENSIONS

(75) Inventor: Irving Boime, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 07/771,262

(22) Filed: Oct. 4, 1991

(51) Int. Cl.[7] .............................. C12P 21/04; A61K 38/00; C07K 16/00; C08G 63/48
(52) U.S. Cl. ........................ 530/399; 435/69.7; 530/324; 525/54.1
(58) Field of Search ........................... 435/69.7; 530/324, 530/399; 525/54.1

(56) References Cited

U.S. PATENT DOCUMENTS

| 4,847,325 | * | 7/1989 | Shadle et al. | 525/54.1 |
| 5,338,835 | | 8/1994 | Boime | 530/398 |

FOREIGN PATENT DOCUMENTS

WO 85/01959   5/1985   (WO).

OTHER PUBLICATIONS

Fuad A. Fares et al., "Design of a long–acting follitropin agonist by fusing the C–terminal sequence of the chorionic gonadotropin beta subunit to the follitropin beta subunit," Proceedings of the National Academy of Sciences of USA, vol. 89, No. 10, May 15, 1992, pp. 4304–4308.

"Polyclonal antibodies against the polypeptide and carbohydrate epitopes of recombinant human choriogonadotropin α–subunit," Molecular and Cellular Endocrinology, vol. 86, issued 1992, W. Chen et al.

"Protein engineering of antibody binding sites: Recovery of specific activity in an anti–digoxin single–chain Fv analogue produced in *Escherichia coli*," Proc. Nat. Acad. Sci. USA, vol. 85, issued Aug. 1988, J.S. Huston et al.

* cited by examiner

Primary Examiner—Gary L. Kunz
Assistant Examiner—Robert S. Landsman
(74) Attorney, Agent, or Firm—Morrison & Foerster LLP

(57) ABSTRACT

The invention provides peptide and protein pharmaceuticals with extended half-lives. The modified peptides and proteins of the invention contain at least two tandem extensions at their C-terminus comprising the carboxy terminal portion of human chorionic gonadotropin. These "CTP units" consist essentially of the native HCG-β sequence from position 112–118 to position 145 or conservative modifications thereof.

5 Claims, 3 Drawing Sheets

HORMONE ANALOGS WITH MULTIPLE CTP EXTENSIONS

This invention was made with Government support under NIH Contract No. HD-9-2922 awarded by the National Institutes of Health. The Government has certain rights in this invention.

TECHNICAL FIELD

The invention relates to pharmaceutical compounds modified so as to extend their in vivo stability. More particularly, the invention concerns modifications of peptides of pharmaceutical significance by tandem extension with the carboxy terminal peptide of human chorionic gonadotropin.

BACKGROUND ART

PCT application WO90/09800, published Sep. 7, 1990, and incorporated herein by reference, describes various modifications of reproductive hormones. In addition, this publication discloses that protein pharmaceuticals and hormones in general may be modified to extend their biological half-lives in vivo by ligation of the carboxy terminal portion of the HCG-β subunit or a variant thereof to the carboxy terminus. The PCT application disclosure does not specifically address tandem extensions with multiple carboxy terminal portions (CTP) of the HCG-β chain. The present invention is directed to such tandem extensions.

Human chorionic gonadotropin (HCG) is one of at least four reproductive hormones in a family which also includes follicle stimulating hormone, luteinizing hormone, and thyroid stimulating hormone. All of these hormones are comprised of α subunits which are identical among the group, and β subunits which differ according to the member of the family. The β subunit of HCG is substantially larger than that of the remaining three hormones in that it contains approximately 34 additional amino acids at the C-terminus referred to herein as the carboxy terminal portion (CTP) which is considered responsible for the comparatively longer serum half-life of hCG as compared to other gonadotropins (Matzuk, M. et al., *Endocrinol* (1989) 126:376). In the native hormone, this CTP extension contains four mucin-like O-linked oligosaccharides.

DISCLOSURE OF THE INVENTION

The invention provides modified peptides and proteins with extended biological half-lives which are characterized by containing, at their carboxy terminus, tandem extensions of at least two CTP sequences. These extended proteins are useful for the same biological functions as their unmodified forms, but permit reduced dosages and other advantages due to their extended biological half-life.

Thus, in one aspect, the invention is directed to a peptide or protein having a biological function in animals, wherein said peptide or protein is modified by a tandem extension at the C-terminus with at least two CTP units. In another aspect, the invention is directed to methods to extend the biological half-life of a peptide or a protein by providing such extensions. In other aspects, the invention is directed to recombinant materials and methods for the construction of the modified peptides of the invention, and to antibodies specifically immunoreactive with them.

MODES OF CARRYING OUT THE INVENTION

Figure 1A:
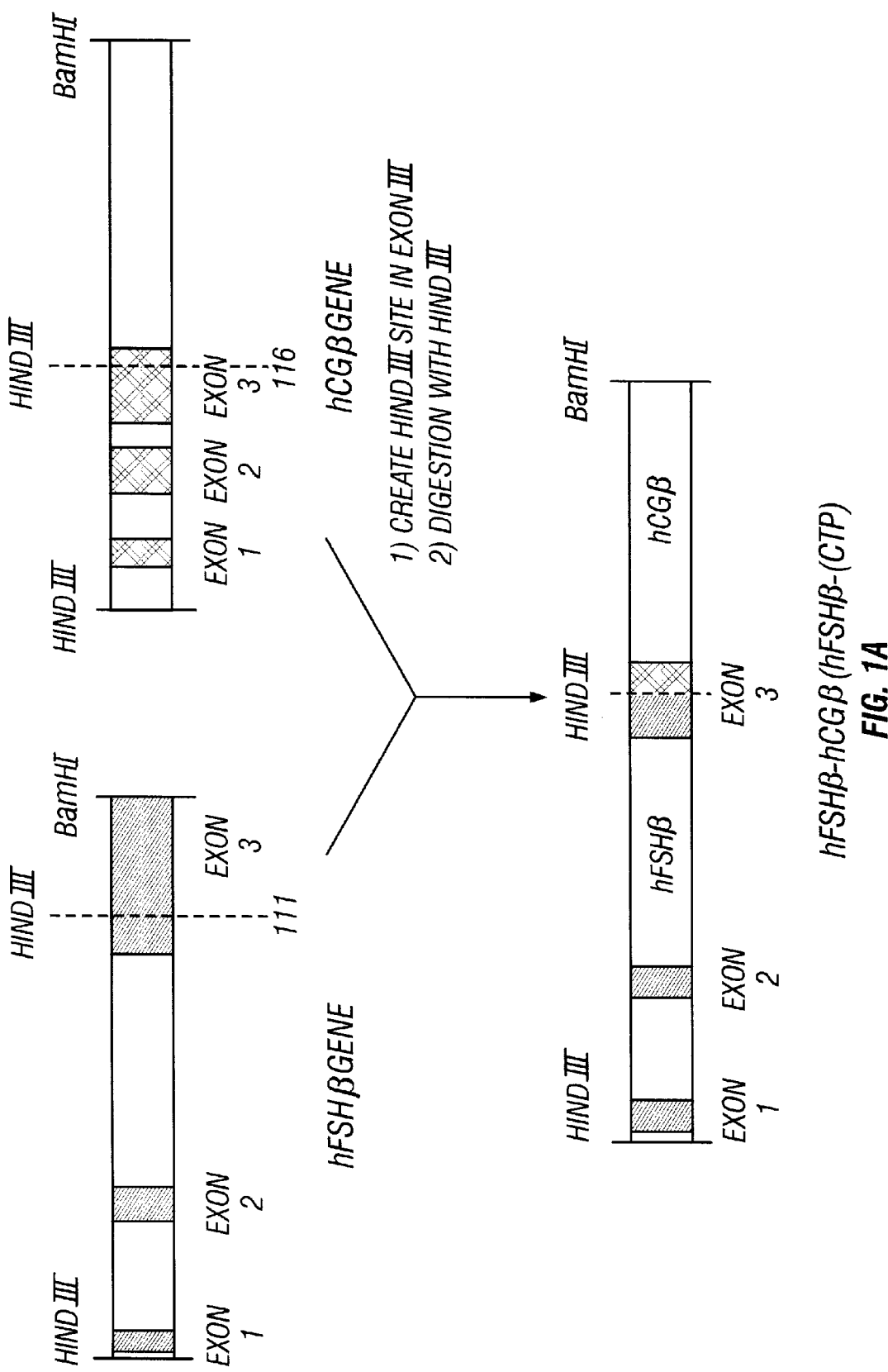
FIGS. 1A–1C show the construction of vectors for the recombinant production of the β subunit of the human follicle stimulating hormone (FSH) containing one or two CTP units as a carboxy terminal extension.

Any peptide or protein of biological significance is subject to modification according to the invention method. Included among such candidates for modification, therefore, are peptide hormones, such as the four human "reproductive" hormones set forth above, especially the β-chains thereof; insulin; human growth hormone; enkephalin; ACTH; glucagon; and the like. Also useful as subjects for the modification of the invention are various growth factors such as insulin-like growth factors; epidermal growth factors; acidic and basic fibroblast growth factors; platelet-derived growth factors; the various colony stimulating factors, such as granulocyte CSF, macrophage-CSF, and the like; as well as the various cytokines such as IL-2, IL-3 and the plethora of additional interleukin proteins; the various interferons; tumor necrosis factor; and the like. Also candidates for the method of the invention are short peptide sequences such as luteinizing hormone releasing hormone (LHRH); somatostatin; growth hormone releasing factor (GHRF); and the endorphins. Additional protein medicaments such as alveolar surfactant proteins; natriuretic factors; adhesins; receptor peptides; receptor binding ligands in general; antibodies and fragments thereof; and any other useful peptide or protein with a desired biological function can be modified according to the methods described herein.

As used herein, the "CTP unit" refers to an amino acid sequence found at the carboxy terminus of human chorionic gonadotropin which extends from amino acid 112–118 to residue 145 at the C-terminus. Thus, each CTP unit used to modify the carboxy terminus of the peptide or protein may independently contain 28–34 amino acids, depending on the N-terminus of the CTP. The "CTP unit" may correspond exactly to the native CTP sequence, or may be a variant wherein 1–5 of the amino acids contained in the sequence is substituted by a conservative analog of the native amino acid residue at that position, and wherein said substitutions taken cumulatively do not result in a substantial change in the stability conferring properties of the CTP unit. "Conservative analog" means, in the conventional sense, an analog wherein the residue substituted is of the same general amino acid category as that for which substitution is made. Amino acids have been classified into such groups, as is understood in the art, by, for example, Dayhoff, M. et al., *Atlas of Protein Sequences and Structure* (1972) 5:89–99. In general, acidic amino acids fall into one group; basic amino acids into another; neutral hydrophilic amino acids into another; and so forth.

More specifically, amino acid residues can be generally subclassified into four major subclasses as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH.

Basic: The residue has a positive charge due to association with H ion at physiological pH and the residue is attracted by aqueous solution so as to seek the surface positions in the conformation of a peptide in which it is contained when the peptide is in aqueous medium at physiological pH.

Neutral/nonpolar: The residues are not charged at physiological pH and the residue is repelled by aqueous solution so as to seek the inner positions in the conformation of a peptide in which it is contained when the peptide is in aqueous medium. These residues are also designated "hydrophobic" herein.

Neutral/polar: The residues are not charged at physiological pH, but the residue is attracted by aqueous solution so as to seek the outer positions in the conformation of a peptide in which it is contained when the peptide is in aqueous medium.

It is understood, of course, that in a statistical collection of individual residue molecules some molecules will be charged, and some not, and there will be an attraction for or repulsion from an aqueous medium to a greater or lesser extent. To fit the definition of "charged," a significant percentage (at least approximately 25%) of the individual molecules are charged at physiological pH. The degree of attraction or repulsion required for classification as polar or nonpolar is arbitrary and, therefore, amino acids specifically contemplated by the invention have been classified as one or the other. Most amino acids not specifically named can be classified on the basis of known behavior.

Amino acid residues can be further subclassified as cyclic or noncyclic, and aromatic or nonaromatic, self-explanatory classifications with respect to the side chain substituent groups of the residues, and as small or large. The residue is considered small if it contains a total of 4 carbon atoms or less, inclusive of the carboxyl carbon. Small residues are, of course, always nonaromatic.

For the naturally occurring protein amino acids, subclassification according to the foregoing scheme is as follows.

Acidic: Aspartic acid and Glutamic acid;

Basic/noncyclic: Arginine, Lysine;

Basic/cyclic: Histidine;

Neutral/polar/small: Glycine, serine, cysteine;

Neutral/nonpolar/small: Alanine;

Neutral/polar/large/nonaromatic: Threonine, Asparagine, Glutamine;

Neutral/polar/large aromatic: Tyrosine;

Neutral/nonpolar/large/nonaromatic: Valine, Isoleucine, Leucine, Methionine;

Neutral/nonpolar/large/aromatic: Phenylalanine, and Tryptophan.

The gene-encoded secondary amino acid proline, although technically within the group neutral/nonpolar/large/cyclic and nonaromatic, is a special case due to its known effects on the secondary conformation of peptide chains, and is not, therefore, included in this defined group.

If the modified peptides of the invention are constructed by modification of the gene, the CTP units will contain only gene encoded amino acid substitutions; however, if the CTP unit is synthesized by standard, for example, solid phase, peptide synthesis methods and ligated, for example, enzymatically, to the C-terminus of the acceptor peptide or protein, non-gene encoded amino acids, such as aminoisobutyric acid (Aib), phenylglycine (Phg), and the like can also be substituted for their analogous counterparts.

These non-encoded amino acids also include, for example, beta-alanine (beta-Ala), or other omega-amino acids, such as 3-amino propionic, 4-amino butyric and so forth, sarcosine (Sar), ornithine (Orn), citrulline (Cit), t-butylalanine (t-BuA), t-butylglycine (t-BuG), N-methylisoleucine (N-MeIle), and cyclohexylalanine (Cha), norleucine (Nle), cysteic acid (Cya) 2-naphthylalanine (2-Nal); 1,2,3,4-tetrahydroisoquinoline-3-carboxylic acid (Tic); mercaptovaleric acid (Mvl); β-2-thienylalanine (Thi); and methionine sulfoxide (MSO). These also fall conveniently into particular categories.

Based on the above definitions,

Sar and beta-Ala and Aib are neutral/nonpolar/small;

t-BuA, t-BuG, N-MeIle, Nle, Mvl and Cha are neutral/nonpolar/large/nonaromatic;

Orn is basic/noncyclic;

Cya is acidic;

Cit, Acetyl Lys, and MSO are neutral/polar/large/nonaromatic; and

Phg, Nal, Thi and Tic are neutral/nonpolar/large/aromatic.

The various omega-amino acids are classified according to size as neutral/nonpolar/small (beta-Ala, i.e., 3-aminopropionic, 4-aminobutyric) or large (all others).

Other amino acid substitutions of those encoded in the gene can also be included in peptide compounds within the scope of the invention and can be classified within this general scheme according to their structure.

It should be noted, of course, that the peptide or protein to which the tandem CTP residues is attached could also be in modified form from that ordinarily occurring biologically, as long as biological activity is retained.

The modified peptides and proteins of the invention may be further modified in ways generally understood to derivatize amino acid sequences, such as phosphorylation, glycosylation, deglycosylation of ordinarily glycosylated forms, modification of the amino acid side chains (e.g., conversion of proline to hydroxyproline) and similar modifications analogous to those post-translational events which have been found to occur generally.

Methods to construct the modified peptide and protein biologically active compounds of the invention are well known in the art. As set forth above, if only gene encoded amino acids are included, the most practical approach at present is to synthesize these materials recombinantly by modification of the DNA encoding the desired peptide. Techniques for site-directed mutagenesis, ligation of additional sequences, and construction of suitable expression systems are all, by now, well known in the art. The DNA encoding the CTP units to be added to the DNA encoding the desired peptide or protein are most conveniently constructed synthetically using standard solid phase techniques, preferably to include restriction sites for ease of ligation, and coupled to the sequence encoding the candidate peptide or protein. If the DNA encoding the candidate peptide or protein is not already a part of an expression system containing suitable control elements for transcription and translation of the included coding sequence, the modified DNA coding sequences are provided with these features. As is well known, expression systems are now available compatible with a wide variety of hosts, including procaryotic hosts such as bacteria and eucaryotic hosts such as yeast, plant cells, insect cells, mammalian cells, avian cells, and the like.

Alternatively, if the candidate biological is a short peptide or if enzymatic transfer of the subunit can be effected, the CTP units of the invention may be synthesized directly using in vitro solid phase peptide synthesis techniques and under these conditions, if desired, the CTP subunit may be modified by analogous amino acids which are not gene encoded.

The resulting modified biologicals will contain at least two CTP units in tandem at their C-terminus. Multiple CTP units containing three or more CTP units are also envisioned and included within the scope of the present invention. As noted above, the CTP units conjugated to the C-terminus in tandem need not be identical with each other. They may vary in length with respect to the N-terminal starting amino acid (position 112–118 of the human chorionic gonadotropin β subunit) and the amino acid substitutions for the native residues, if any, may vary from unit to unit in the tandem sequences included.

Coupled Forms of the Invention Proteins

As is generally known in the art, the modified peptides and proteins of the invention may be coupled to labels, drugs, targeting agents, carriers, solid supports, and the like, depending on the desired application. The labeled forms of the modified biologicals may be used to track their metabolic fate; suitable labels for this purpose include, especially, radioisotope labels such as iodine 131, technetium 99, indium 111, and the like. The labels may also be used to mediate detection of the modified proteins or peptides in assay systems; in this instance, radioisotopes may also be used as well as enzyme labels, fluorescent labels, chromogenic labels, and the like. The use of such labels is particularly helpful if the peptide or protein is itself a targeting agent such as an antibody or a receptor ligand.

Conversely, if the modified peptide or protein is a targeting ligand, primarily, and is relatively free of metabolism-altering activity, the modified compound of the invention may be conjugated to an appropriate drug, such as an antiinflammatory drug, an antibiotic, a toxin, and the like. The modified compounds of the invention may also be coupled to carriers to enhance their immunogenicity in the preparation of antibodies specifically immunoreactive with these new modified forms. Suitable carriers for this purpose include keyhole limpet hemocyanin (KLH), bovine serum albumin (BSA) and diphtheria toxoid, and the like. Standard coupling techniques for linking the modified peptides of the invention to carriers, including the use of bifunctional linkers, can be employed.

Similar linking techniques, along with others, may be employed to couple the modified peptides and proteins of the invention to solid supports. When coupled, these modified peptides and proteins can then be used as affinity reagents for the separation of desired components with which specific reaction is exhibited.

Finally, the modified peptides and proteins of the invention may be used to generate antibodies specifically immunoreactive with these new compounds. These antibodies are useful in a variety of diagnostic and therapeutic applications, depending on the nature of the biological activity of the unmodified peptide or protein.

The modified peptides or proteins of the invention are formulated and administered using methods comparable to those known for the unmodified peptide or protein corresponding to the modified form. Thus, formulation and administration methods will vary according to the candidate unmodified form. However, the dosage level and frequency of administration may be reduced as compared to the unmodified form in view of the extended biological half life of the modified peptide or protein.

The following examples are intended to illustrate but not to limit the invention.

EXAMPLE 1

Preparation of Human β Subunit with Two CTP Unit Tandem Extensions

Figure 1B:
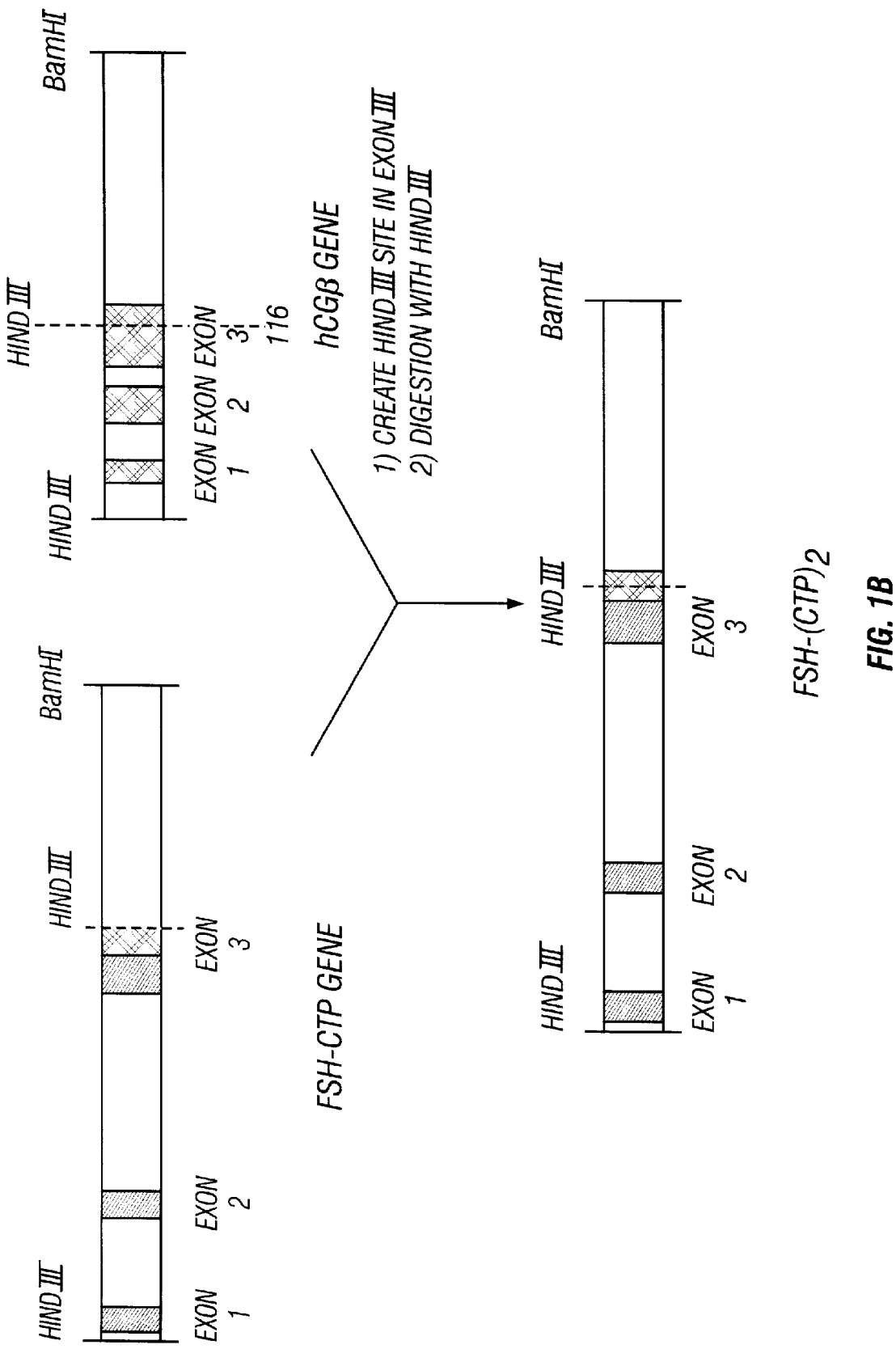

FIGS. 1A and 1B show the construction of an expression vector wherein the β-chain of human FSH is modified to include two CTP units. As shown in FIG. 1B, the HindIII site at the 3'-terminus of the human FSH-β subunit, extended by one CTP unit is used to couple the CTP unit from the 3' terminus of the human HCG-β gene to obtain the extended β subunit. The hFSH-β (CTP)$_2$ gene is then ligated into the expression vector pM$^2$ to obtain an expression system capable of producing the extended form of the FSH-β chain in mammalian cells. The construction of the host expression vectors is described by Matzuk, M. M. et al., *Proc Natl Acad Sci USA* (1987) 84:6354–6358; Matzuk, M. M. et al., *J Cell Biol* (1988) 106:1049–1059.

In more detail, to create hFSHβ chimera bearing a single unit of the O-linked terminal region of hCGβ subunit (hFSHβ (CTP)) a HindIII site was created in the stop codon of hFSHβ gene at codon 111 and in the hCGβ gene at codon 118 (FIG. 1A). The HindIII—HindIII fragment from the hFSHβ gene was ligated in frame to the CGβ BamHI-HindIII fragment. This chimera (hFSHβ(CTP)) contained a ser$^{118}$ to Ala$^{118}$ change at the ligation point, which was corrected by oligonucleotide-directed mutagenesis. The chimera containing two tandem CTP repeats (hFSHβ (CTP)$_2$ was constructed by creating a new HindIII site in the stop codon of the hFSHβ(CTP) chimera (FIG. 1B). The HindIII—HindIII fragment was ligated to the BamHI-HindIII fragment from hCGβ. The generated ala codon can be reconverted to a serine codon as described above.

Figure 1C:
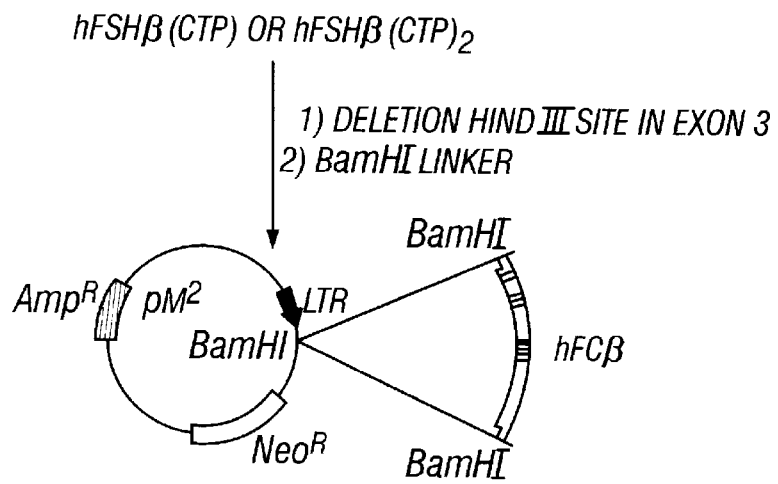

To insert hFSHβ(CTP) or hFSHβ(CTP)$_2$ genes into the eucaryotic expression vector pM$^2$, the HindIII sites at the 5' ends were converted to BamHI sites using Klenow and BamHI oligonucleotide linker (FIG. 1C), and the BamHI—BamHI fragments containing the hFSHβCTP or hFSHβ (CTP)$_2$ genes were inserted into the BamHI site in pM$^2$. The correct orientation was confirmed by restriction enzyme analysis and the entire sequence of exon III was sequenced to confirm the specificity of the mutagenesis.

EXAMPLE 2

Effect of CTP Tandem Extensions

Figure 2:
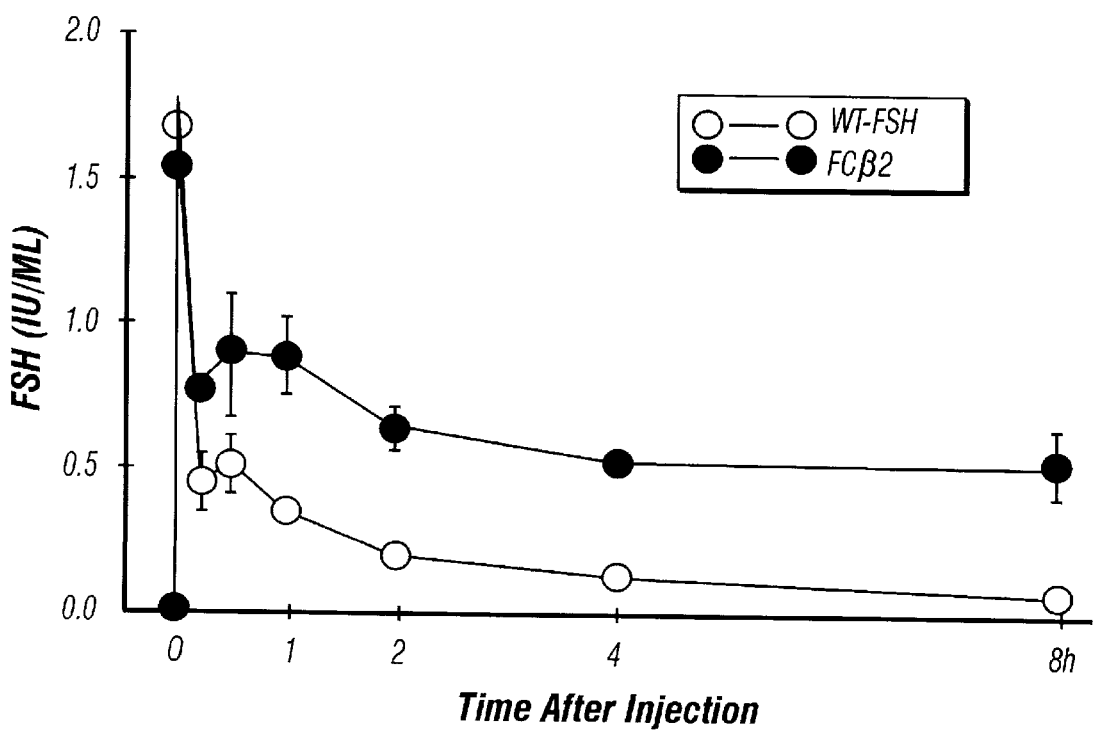
FIG. 2 shows the enhancement of biological stability of FSH containing the two unit CTP C-terminal extension of its β subunit as compared to wild-type FSH.

The human FSH containing the β subunit extended by two CTP units prepared as set forth in Example 1 above was injected into rats. 24 Sprague-Dawley female rats were used in the study. 12 rats were each injected with 10 IU unmodified FSH formulated in MEM medium; 12 rats were injected with 10 IU FSH comprising hFSHβ(CTP)$_2$ formulated in MEM medium. Serum was withdrawn immediately and several times during the first hour, and then after 2, 4 and 8 hours. The serum was assayed using standard radioimmunoassay techniques for FSH hormone. The results are shown in FIG. 2.

As there shown, while the amount of unmodified FSH in the serum declined from about 0.5 IU/ml to less than 0.05 IU/ml over an 8 hour period, the modified FSH of the invention containing two CTP units remains substantially unchanged over this time period declining from about 0.8 IU/ml to about 0.5 IU/ml.

What is claimed is:

1. A modified peptide or protein wherein said peptide or protein has biological activity, wherein said modification comprises an extension at the C-terminus consisting essentially of two or more tandem units wherein each unit independently consists of amino acid sequences found natively at positions 112–118 to position 145 of the beta subunit of human chorionic gonadotropin.

2. The modified peptide or protein of claim 1 wherein said peptide or protein is a hormone or a subunit thereof.

3. The modified protein or peptide of claim 1 wherein the peptide or protein is a growth factor.

4. The modified peptide or protein of claim 1 wherein the peptide or protein is a cytokine.

5. The modified peptide or protein of claim 2 wherein said peptide or protein is luteinizing hormone (LH) or a follicle stimulating hormone (FSH).

* * * * *